(12) United States Patent
Barton et al.

(10) Patent No.: US 7,560,692 B2
(45) Date of Patent: Jul. 14, 2009

(54) METHOD OF TEM SAMPLE PREPARATION FOR ELECTRON HOLOGRAPHY FOR SEMICONDUCTOR DEVICES

(75) Inventors: Keith E. Barton, Hyde Park, NY (US); Steven H. Boettcher, Fishkill, NY (US); John G. Gaudiello, Poughkeepsie, NY (US); Leon J. Kimball, Montgomery, NY (US); Yun-Yu Wang, Poughquag, NY (US)

(73) Assignees: International Business Machines Corporation, Armonk, NY (US); Dongbu Electronics Co., Ltd. (KR)

( * ) Notice: Subject to any disclaimer, the term of this patent is extended or adjusted under 35 U.S.C. 154(b) by 243 days.

(21) Appl. No.: 11/617,386

(22) Filed: Dec. 28, 2006

(65) Prior Publication Data

US 2008/0156987 A1 Jul. 3, 2008

(51) Int. Cl.
*G01N 1/32* (2006.01)
*G01N 23/04* (2006.01)

(52) U.S. Cl. .................. 250/307; 250/306; 250/310; 250/311; 250/492.2; 250/492.3

(58) Field of Classification Search .......... 250/307, 250/311, 397, 452.21, 309, 492.2; 438/14, 438/98, 197, 13
See application file for complete search history.

(56) References Cited

U.S. PATENT DOCUMENTS 5,935,870 A    8/1999   Lee
6,140,652 A *  10/2000  Shlepr et al. ........... 250/440.11
6,335,533 B1 * 1/2002   Morales et al. .......... 250/492.2
6,646,259 B2   11/2003  Chang et al.

(Continued)

FOREIGN PATENT DOCUMENTS

WO    WO 00/10020    2/2000

OTHER PUBLICATIONS

The specification pages for Vishay brand M-Bond Adhesive: http://www.vishay.com/company/brands/measurements-group/guide/a110/acc/mbae15.htm, most recently updated Jan. 15, 2005.*

(Continued)

*Primary Examiner*—Jack I Berman
*Assistant Examiner*—Nicole Ippolito Rausch
(74) *Attorney, Agent, or Firm*—Scully, Scott, Murphy & Presser, P.C.; Steven Capella, Esq.

(57) ABSTRACT

A high quality electron microscopy sample suitable for electron holography is prepared by forming markers filled with TEOS oxide and by repeatedly applying multiple coats of an adhesive followed by a relatively low temperature cure after each application. The TEOS oxide marker is readily visible during the polish, has a similar polish rate as a semiconductor material, and reduces contamination during sample preparation. The repeated application of adhesives separated by relatively low temperature cures increases the adhesive strength of the adhesive material to the semiconductor material without making it too brittle. This results in an improved control and yield of the sample preparation process.

10 Claims, 3 Drawing Sheets

U.S. PATENT DOCUMENTS

| | | |
|---|---|---|
| 6,884,641 B2 | 4/2005 | Bruley et al. |
| 7,214,935 B2 * | 5/2007 | Bauer et al. ................. 250/307 |
| 7,271,073 B2 * | 9/2007 | Van Haren et al. .......... 438/401 |
| 2002/0153478 A1 * | 10/2002 | Hsin ..................... 250/227.14 |
| 2005/0285106 A1 * | 12/2005 | Kane et al. .................... 257/48 |
| 2006/0003546 A1 * | 1/2006 | Klipp et al. ................. 438/431 |
| 2007/0113973 A1 * | 5/2007 | Marszalek et al. .......... 156/292 |
| 2008/0067387 A1 * | 3/2008 | Mouttet ..................... 250/311 |
| 2008/0206546 A1 * | 8/2008 | Waki ....................... 428/315.5 |

OTHER PUBLICATIONS

Rau, W. D., et al., "Two-Dimensional Dopant Profiling of Deep Submicron MOS Devices by Electron Holography", IEDM 98-713, IEEE 0-7803-4774-9/98, 1998, pp. 27.1.1-27.1.4.

Chakraborty, Partha Sarathi, et al., "Electron Holographic Characterization of Ultra-Shallow Junctions in Si for Nanoscale MOSFETs", IEEE Transactions on Nanotechnology, vol. 2, No. 2, Jun. 2003.

* cited by examiner

METHOD OF TEM SAMPLE PREPARATION FOR ELECTRON HOLOGRAPHY FOR SEMICONDUCTOR DEVICES

FIELD OF THE INVENTION

The present invention relates to characterization methods for transmission electron microscopy, and particularly to preparation of a TEM (transmission electron microscopy) sample for high resolution TEM holography.

BACKGROUND OF THE INVENTION

Since Dennis Gabor, a Hungarian-British physicist invented electron holography in 1947, many advances have been made in the field of electron microscopy. In electron holography, the phase component and the amplitude component of the information are separated by splitting the electron beam in a transmission electron microscope into two parts with a biprism and combining them after at least one part of the beam passes through a sample. By processing the information to reconstruct an object that a part of the beam went through, an image of the sample is reconstructed.

In principle, any physical quantity that affects the phase of an electron beam may be measured and reconstructed by electron holography. Examples of physical quantities that can be measured in electron holography include mechanical features of atoms such as the shapes of nanocrystals or nanoscale voids, electrical field such as ferroelectric materials generate, and magnetic field such as ferromagnetic materials generate. In the semiconductor industry, electron holography has been shown to be valuable in mapping p-n junction characteristics in semiconductor devices, such as a MOSFET, with high spatial resolution. Due to the remarkable advances in this field, commercial electron holography equipments and textbooks on this subject are readily available.

Unlike other applications of transmission electron microscopy, however, electron holography requires an extremely careful sample preparation. The quality of data that can be extracted from a sample depends on the sample preparation method. This is because the phase component of the information used in electron holography is more sensitive to the surface conditions of a sample than other information, such as intensity information, used in other applications of transmission electron microscopy. For example, while regular TEM sample preparation may utilize ion milling, in which energetic ions remove the material while generating some surface damage, to generate a TEM sample of acceptable quality for other TEM applications, the structural degradation of the surface of such samples introduces a significant amount of noise into electron holography images.

Therefore, mechanical polishing has been the method of choice for sample preparation despite the laborious nature of the process. One of the difficulties in the sample preparation is the control of thickness, especially toward the end of the polishing process. Once the sample is overthinned, the sample is no longer suitable for electron holography. According to a commonly used method of preparing a sample for electron holography, the thickness of the sample is checked frequently to insure that overpolishing, and consequently overthinning of the sample does not occur. This requires intensive intervention during the polishing process.

Another difficulty in the sample preparation is that the adhesive material that protects the upper surface of the sample area tends to get rounded during the polishing and also tends to fall apart during the sample preparation.

These difficulties make a sample preparation process for electron holography laborious and unpredictable.

Therefore, there exists a need for a method and structure for self-limiting the thickness of a polished electron microscopy sample, and especially for electron holography sample preparation.

There also exists a need for a method of holding the adhesive material over the top surface of the sample without delamination.

There also exists a need for a method of providing a high quality sample for other transmission electron microscopy methods to provide an enhanced image with better resolution than normal TEM samples.

SUMMARY OF THE INVENTION

According to the present invention, at least two marker trenches are formed on the front surface of a sample and a filler material fills the marker trenches. The width of the marker trenches is identical to the width of the region of interest for inspection in the sample. The top of the sample is polished down to the level containing the region of interest and at least two markers are thereby formed. A suitable filler material with good visibility and an appropriate polish rate compared to the sample is used to fill the marker trenches.

According to a preferred embodiment of the present invention, a TEOS (tetra-ethyl-ortho-silicate) oxide is provided as a filler material for the purpose of sample preparation for electron holography. Specifically, a TEOS oxide is used to fill the marker trenches formed by etching the top surface of the electron holography sample.

According to the present invention, a method of preparing a sample for electron microscopy by utilizing an oxide for forming markers is provided, which comprises:
etching at least two marker trenches on the top surface of a sample;
filling the at least two marker trenches with filler material;
delayering the sample to the upper surface of a region of interest;
applying at least one coat of adhesive to the delayered sample; and
polishing both sides of the sample.

Preferably, at least two markers have a substantially rectangular cross-sectional opening and have a width in the range from about 100 nm to about 1,000 nm, a length in the range from about 500 nm to about 10,000 nm, and a depth in the range from about 1,000 nm to about 50,000 n. More preferably, at least two markers have a width in the range from about 200 nm to about 400 nm, a length in the range from about 1,000 nm to about 4,000 nm, and a depth in the range from about 5,000 nm to about 10,000 nm.

The filler material may be a metal such as W, TiN, TaN, or Cu. Alternatively, the filler material is a dielectric layer such as silicon oxide, silicon nitride, or silicon oxynitride. Preferably, the filler material is a silicon oxide. In a preferred embodiment of the present invention, the silicon oxide is a TEOS oxide. The TEOS oxide may be deposited by any of the chemical vapor deposition methods that covert the TEOS into an oxide film. Preferably, the TEOS oxide is deposited by plasma-enhanced chemical vapor deposition (PECVD).

Preferably, the thickness of the sample after polishing is in the range of 10 nm to 500 nm and more preferably in the range from about 100 nm to about 200 nm.

After the formation of the marker layers, an adhesive, e.g., a resin cement, is applied to the top surface of the sample and cured. The sample is polished mechanically from both sides until the sidewalls of the markers are exposed, at which point, the polish rate drastically drops. Therefore, the polishing self-stops on both sidewalls of the markers. The remaining sample, which is only about 10 nm~500 nm thick by now, is mounted for electron holography.

According to the present invention, a method of holding an adhesive material over the top surface of the sample without delamination is disclosed. Specifically, an adhesive, preferably a resin cement, is applied at least twice, wherein each coat of adhesive is cured at a temperature from about 70° C. to about 130° C. after each application.

The methods according to the present invention may be utilized for preparing a sample for electron holography or for preparing a sample for high quality transmission electron microscopy.

According to the present invention, a method of preparing a sample for electron microscopy by utilizing multiple coats of adhesive followed by curing at a relatively low temperature is provided, which comprises:

etching at least two marker trenches on the top surface of a sample;

filling said at least two marker trenches with a fill material;

delayering the sample to the upper surface of a region of interest;

applying a first coat of an adhesive to the delayered surface of the sample and curing the first coat at a temperature from about 70° C. to about 130° C.;

applying a second coat of the adhesive to the cured first coat and curing the second coat at a temperature from about 70° C. to about 130° C.;

polishing both sides of the sample; and removing the adhesive from said sample.

Preferably, the adhesive is a resin cement. The curing of the first coat is performed for a time in the range from about 15 minutes to about 120 minutes. The curing of the second coat is also performed for a time in the range from about 15 minutes to about 120 minutes.

Preferably, a third coat of the adhesive is applied to the delayered surface of the sample. The third coat is cured at a temperature from about 70° C. to about 130° C.

Preferably, the fill material is an oxide and more preferably, a TEOS oxide.

According to the present invention, the sample is preferably a semiconductor sample that contains at least one semiconductor device. The sample contains at least one metal wiring level and the sample is delayered prior to the etching of the at least two markers such that the sample contains no more than one metal wiring level. Also, preferably, the width of the sample between the two sides is in the range from about 50 nm to about 300 nm.

Preferably, the thickness of the sample is in the range from about 10 nm to about 500 nm, more preferably in the range from about 100 nm to about 200 nm after the polishing of both sides of the sample.

According to the present invention, a method of preparing a sample for electron microscopy is provide in which TEOS oxide is utilized for filling marker trenches and multiple coats of adhesive are utilized followed by curing at a relatively low temperature after each coat. According to this method, both of the inventive elements of the present invention are utilized for electron microscopy. The resulting sample is a high quality sample suitable for electron holography.

BRIEF DESCRIPTION OF THE DRAWINGS

FIG. 2A also corresponds to cross-sectional views of the electron microscopy sample in FIGS. 3-6 along the horizontal plane A-A' of FIGS. 3-6.

DETAILED DESCRIPTION OF THE INVENTION

According to the present invention, an electron microscopy sample is prepared. Preferably, the electron microscopy sample is a semiconductor sample containing a semiconductor device. While the present invention is applicable to non-semiconductor samples, the present invention is described using a semiconductor sample as an example. Application of the present invention to non-semiconductor samples is explicitly contemplated herein.

Figure 1A:
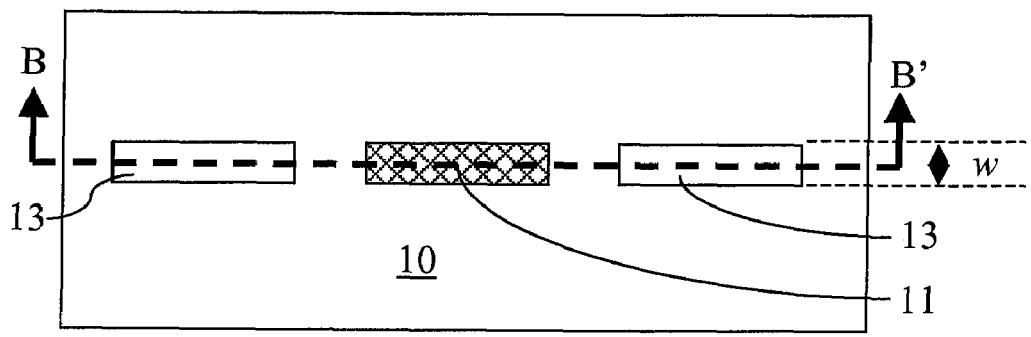
FIGS. 1A and 2A are sequential cross-sectional views of an electron microscopy sample according to the present invention along the horizontal plane A-A' of FIG. 1B or 2B.
Figure 1B:
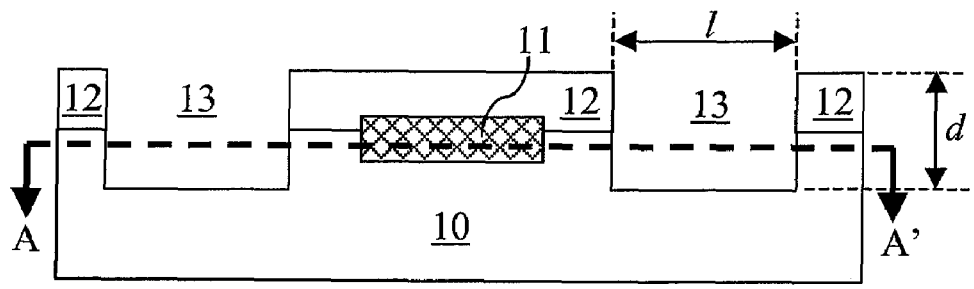
FIGS. 1B and 2B are sequential cross-sectional views of an electron microscopy sample according to the present invention along a vertical plane B-B' of FIG. 1A or 2A.

Referring to FIGS. 1A and 1B, cross-sectional views of an exemplary electron microscopy sample according to the present invention are shown. FIG. 1A is a horizontal cross-sectional view of the exemplary electron microscopy sample. FIG. 1B is a vertical cross-sectional view of the exemplary electron microscopy sample. The cross-section for FIG. 1A is taken along the line A-A' of FIG. 1B. The cross-section for FIG. 1B is taken along the line B-B' of FIG. 1A. FIGS. 1A and 1B show a semiconductor substrate 10, a region of interest 11 that contains at least one semiconductor device, a back-end-of-line (BEOL) dielectric stack 12 that may contain one metal wiring level, and possibly multiple metal wiring levels, two marker trenches 13 with a width w, a length l, and a depth d. A typical thickness for the semiconductor substrate 10 is about 800 microns and a typical thickness of the BEOL dielectric stack 12 depends on the number of wiring levels within the BEOL dielectric stack 12, in which each BEOL wiring level has a thickness from about 200 nm to about 2,000 nm. If an original semiconductor sample contains multiple metal wiring levels, the sample is preferably delayered to remove some of the metal wiring levels so that no more than one metal wiring level is present before the formation of the marker trenches 13 to facilitate sample preparation. Preferably, the region of interest 11 has a length in the range from about 1,000 nm to about 4,000 nm, a width in the range from about 70 nm to about 300 nm, and a height in the range from about 70 nm to about 300 nm. More preferably, the region of interest 11 has a length in the range from about 1,500 nm to about 3,000 nm, a width in the range from about 100 nm to about 200 nm, and a height in the range from about 100 nm to about 200 nm.

The marker trenches 13 are formed by removing material from the BEOL dielectric stack 12 and from the semiconductor substrate 10. Preferably, a focused ion beam is utilized to remove the material and to form the marker trenches 13. At least two marker trenches 13 are formed. The at least two marker trenches 13 are placed around the region of interest 11 to help identify the location of the region of interest 11 during the sample preparation. Preferably, the at least two marker trenches 13 have a substantially rectangular cross-sectional opening and have a length in the range from about 1,000 nm to about 4,000 nm, a width in the range from about 70 nm to about 300 nm, and a depth in the range from about 1,000 nm to about 50,000 nm. More preferably, the at least two marker trenches 13 have a length in the range from about 1,500 nm to about 3,000 nm, a width in the range from about 100 nm to about 200 nm, and a depth in the range from about 5,000 nm to about 10,000 nm.

Figure 2A:
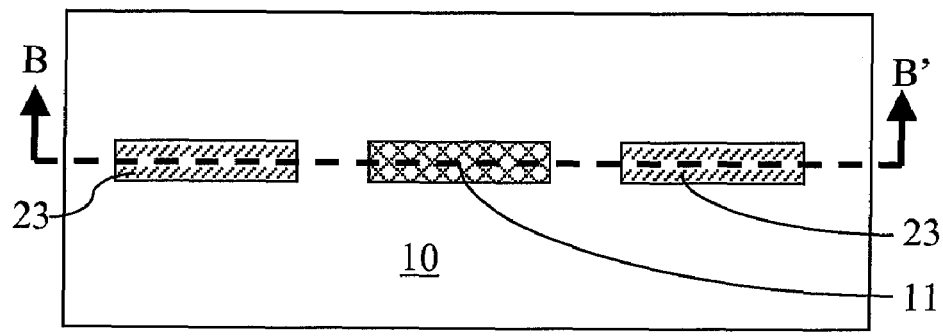
Figure 2B:
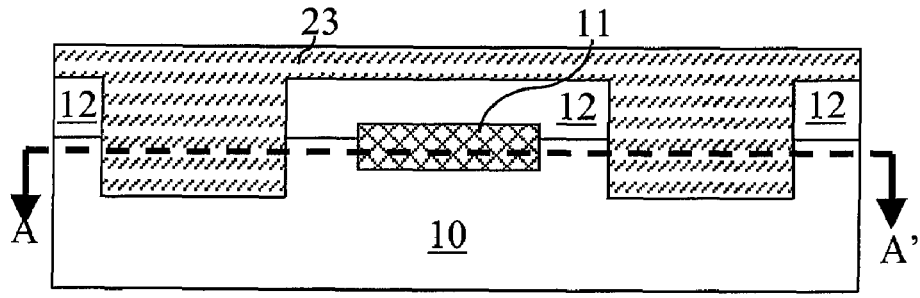

According to the present invention, the marker trenches 13 are filled with a filler material 23 as shown in FIGS. 2A and 2B, which respectively correspond to the cross-sections shown in FIGS. 1A and 1B after the oxide fill. The thickness of the filler material 23, as measured over the BEOL dielectric stack 12, is thick enough to completely fill the marker trenches. Preferably, the thickness of the filler material 23 is in the range from about 50 nm to about 100,000 nm. More preferably, the thickness of the filler material 23 is in the range from about 50 nm to about 1,000 nm.

Preferably, the filler material 23 is a silicon oxide. In a preferred embodiment of the present invention, the silicon oxide is a TEOS oxide. TEOS (tetra-ethyl-ortho-silicate; $Si(OCH_2CH_3)_4$) is a precursor for chemical vapor deposition of silicon dioxide. The TEOS oxide may be doped with other dopants such as boron, phosphorus, or fluorine. The TEOS oxide may be deposited by various deposition methods such as low pressure chemical vapor deposition (LPCVD), high density plasma (HDP) deposition, or plasma enhanced chemical vapor deposition (PECVD). Preferably, the TEOS oxide is deposited by plasma enhanced chemical vapor deposition (PECVD). Other oxides, such as a BTBAS oxide, which utilize BTBAS (bis(tertiary-butylamino) silane) as the precursor for a CVD reaction instead of TEOS, may be used instead either without doping or with doping.

To prevent overthinning of the sample, a suitable filler material 23 needs to have a slightly lower polish rate than a representative sample material to slow down the polishing once the sidewalls of the markers are exposed through polishing. Also, the polish rate of the filler material 23 also needs to be not excessively low to prevent the creation of steps around the markers, that is, by not removing the marker material while removing the sample material from around the markers.

Therefore, it is preferred that the filler material has somewhat lower polish rate than the most representative material of the sample. For example, a silicon oxide or silicon nitride filler material in a silicon sample satisfies this requirement. The polish rate of a silicon sample is higher than the polish rate of silicon oxide or silicon nitride but only by about an order of magnitude or less.

Any material possessing the above properties may be used as a filler material. Exemplary filler materials include silicon oxide, silicon nitride, silicon oxynitride, high-K dielectric, and metals such as platinum.

Of the various filler materials that were tested in a laboratory testing, silicon oxide exhibited excellent characteristics as a filler material due to the relative polish rate compared to typical semiconductor material, optical visibility, and lack of sample contamination problems. TEOS oxide has extensively been used as a filler material with consistent results.

Figure 3:
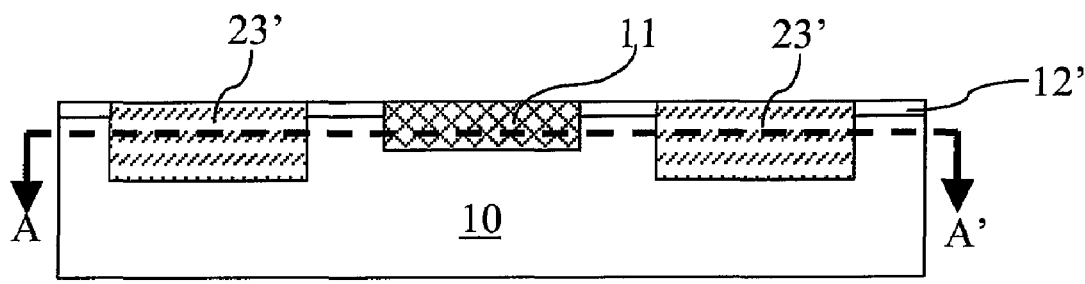
FIGS. 3-6 are sequential cross-sectional views of an electron microscopy sample according to the present invention along a vertical plane that is equivalent to B-B' of FIGS. 1A and 2A.

After filling the marker trenches 13 with a filler material 23, preferably with a TEOS oxide, the top portion of the filler material 23 over the BEOL dielectric stack 12 and a portion of the BEOL dielectric stack 12 are polished such that the top surface of the region of interest 11 is exposed as shown in FIG. 3. Typically, the height of the remaining BEOL dielectric stack 12' after this polish is in the range from about 25 nm to about 200 nm, and preferably from about 40 nm to about 80 nm. The remaining portion of the filler material 23 after the polish forms markers 23' That may be utilized to locate The region of interest 11 during the polish of the sides at a later stage in the sample preparation. The corresponding horizontal cross-sectional view along the plane A-A' in FIG. 3 is identical to the previous horizontal cross-sectional view, FIG. 2A except for the replacement of the filler material 23 with markers 23' since polishing does not change the structure below the remaining BEOL dielectric stack 12'.

Figure 4:
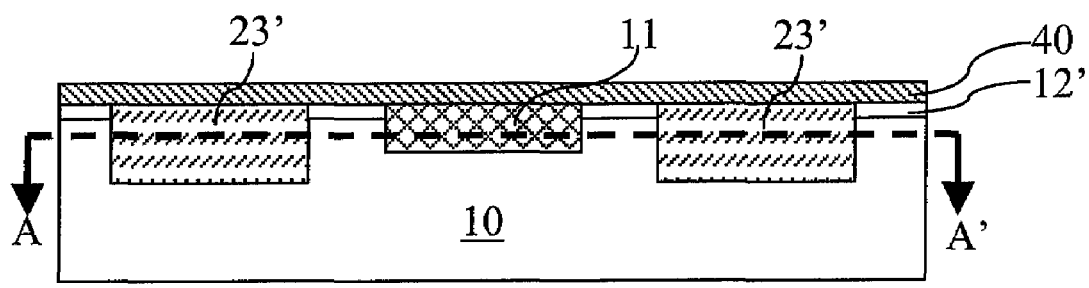

According to the present invention, repeated coats of an adhesive are applied to the top side of the sample, which is the surface of the remaining BEOL dielectric stack 12', with a cure at a relatively low temperature after each application of the adhesive layers. FIG. 4 shows a vertical cross-sectional view of the sample after the application of the first coat 40 of the adhesive. The thickness of each coat of the adhesive, including the thickness of the first coat 40, is from about 1,000 nm (1 micron) to about 20,000 nm (20 micron), and preferably from about 5,000 nm (5 micron) to about 10,000 nm (10 micron).

Preferably, the adhesive is a resin cement. A resin cement is a monomer or monomer/polymer system that develops adhesive strength within a relative fast curing time (on the order of 10 minutes) and is widely used as a dental luting agent. A resin cement is also used in cementation of restorations or orthodontic brackets to the teeth. Examples of commercially available resin cements include Vishay M-bond (manufactured by Vishay Intertechnology Inc.), Tokuyama M-Bond (manufactured by Tokuyama), Super-Bond C&B (manufactured by Sunmedical). Mean tensile bond strengths 10 minutes after application typically vary from about 2 MPa to about 10 MPa. After curing for 24 hours at room temperature, mean tensile bond strength typically ranges from about 8 MPa to about 18 MPa depending on the remaining resin monomer percentage at the end of curing. Curing at a higher temperature generally accelerates the curing process.

According to the present invention, the first coat 40 of the adhesive is cured at a relatively low temperature from about 70° C. to about 130° C., more preferably from about 85° C. to about 115° C., and most preferably close to about 100° C. This contrasts with the prior art method of curing the adhesive at a temperature close to about 200° C., and at a minimum temperature above 150° C. Preferably, the curing of the first coat 40 of the adhesive is performed for a time in the range from about 15 minutes to about 120 minutes.

Figure 5:
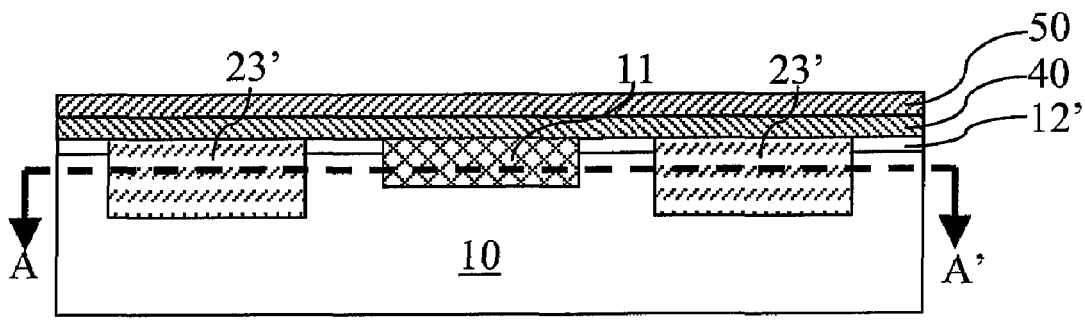

According to the present invention, a second coat 50 of the adhesive is applied to the cured first coat 40 of the adhesive as shown in FIG. 5. The second coat 50 of the adhesive is cured at a relatively low temperature from about 70° C. to about 130° C., more preferably from about 85° C. to about 115° C., and most preferably close to about 100° C. The application of a second coat 50 of the adhesive contrasts with the prior art, wherein only one coat of an adhesive is used for a sample preparation.

Figure 6:
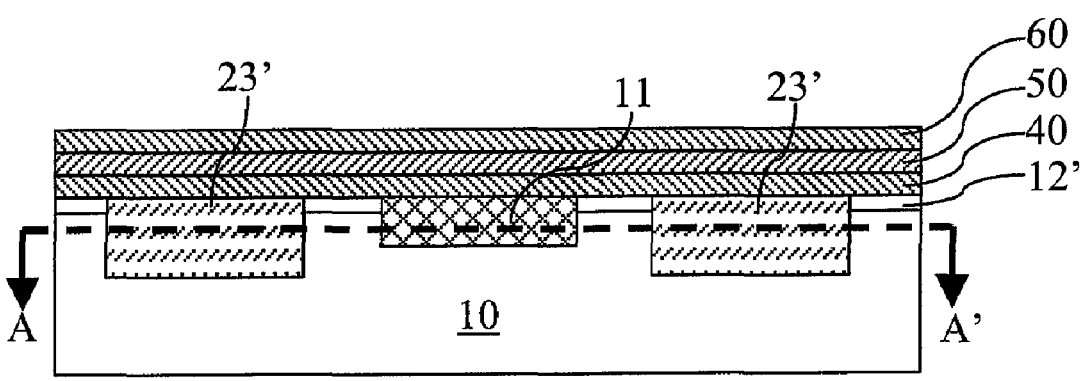

Optionally, a third coat 60 of the adhesive is applied to the cured second coat 50 of the adhesive as shown in FIG. 6. The third coat 60 of the adhesive is cured at a relatively low temperature from about 70° C. to about 130° C., more preferably from about 85° C. to about 115° C., and most preferably close to about 100° C.

A feature of the present invention is the repeated application of a coat of an adhesive with curing of the coat at a relatively low temperature between applications. During the research leading to the present invention, various methods for coating and curing adhesives were tried. A single application of a thick coat of an adhesive did not produce as good adhesion of the adhesive material to the sample as multiple coats of the same adhesive wherein the total coat thickness is the same as that of the thick coat, especially among resin cements. Furthermore, curing of each coat of the adhesive either at the room temperature or at a higher temperature above about 150° C. resulted in no appreciable improvement in the adhesion strength or brittleness of the cured adhesive that resulted in a breakage or a delamination during a subsequent polish. At least two coats of adhesive followed by a cure at a temperature in the range from about 70° C. to about 130° C. was necessary to substantially improve adhesion strength of the adhesive to the sample.

Figure 7A:
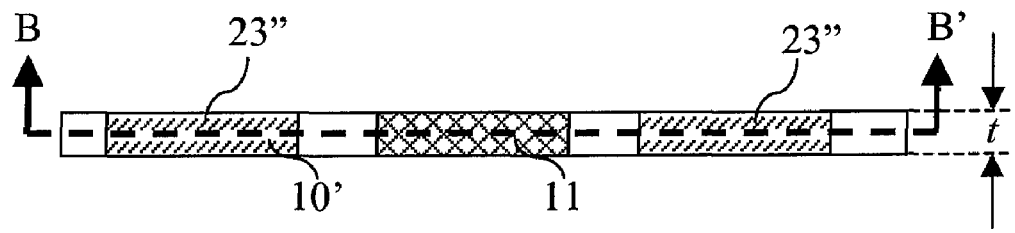
FIGS. 7A and 8A are sequential cross-sectional views of an electron microscopy sample according to the present invention along the horizontal plane A-A' of FIG. 7B or 8B.

Thereafter, the sample is polished mechanically from both sides until the sides of the region of interest 11 are exposed as shown in FIG. 7A. During the polish of the sides of the sample, the cured adhesive material, represented by the three coats (40, 50, and 60) of the adhesive in FIG. 6 protects the upper surface of the region of interest 11 so that rounding of the sample at the top surface is prevented. As mentioned above, the improved matching of the polish rates between the material for the markers 23' and the material comprising the semiconductor substrate 10 improves the uniformity of the thickness between the polished marker, or the thinned marker 23" and the thinned semiconductor substrate 10'. Furthermore, the improved adhesion of the cured coats (40, 50, and 60) of the adhesive prevents a delamination of the adhesive material from the sample during the polish, which is often the case with sample preparation methods according to the prior art.

Figure 7B:
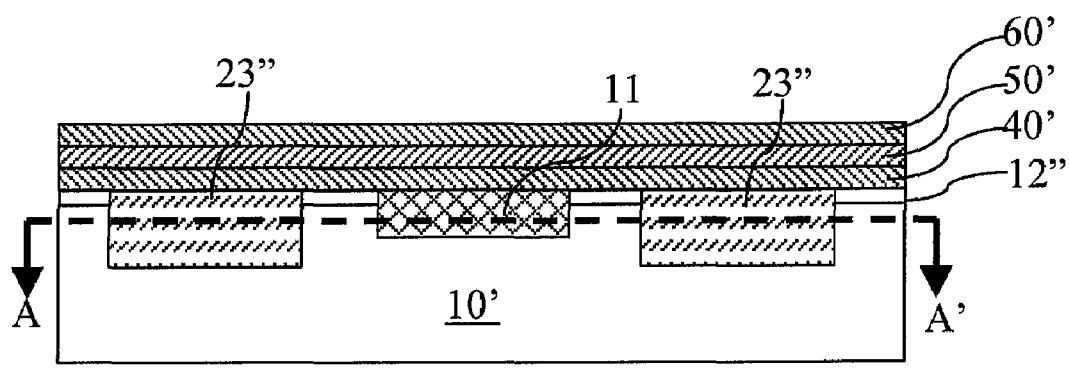
FIGS. 7B and 8B are sequential cross-sectional views of an electron microscopy sample according to the present invention along a vertical plane B-B' of FIG. 7A or 8A.

FIG. 7B, which is the vertical cross-sectional view of the sample along the plane B-B' in FIG. 7A, is at this point identical to the prior vertical cross-sectional view, FIG. 6, since the polishing is done only from the sides of the sample. The resulting structure, as shown in FIGS. 7A and 7B, contains the region of interest 11, and the thinned semiconductor substrate 10', the thinned markers 23", the thinned remaining BEOL dielectric stack 12", the first coat 40' of the adhesive, the second coat 50' of the adhesive, and the third coat 60' of the adhesive. The thickness of the thinned layers, labeled "t" in FIG. 7A, is identical to the thickness of the region of interest, which is typically within the range from about 10 nm to about 500 nm, preferably within the range from about 100 nm to about 200 nm, after polishing of both sides of the sample.

Figure 8A:
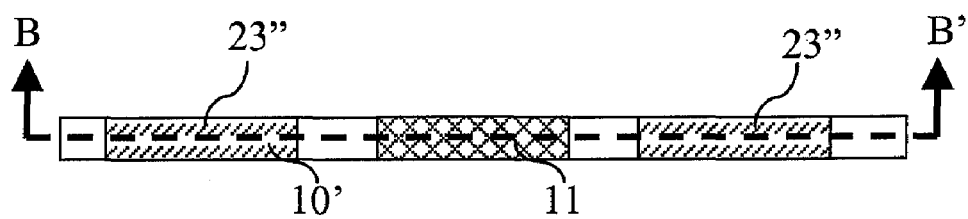
Figure 8B:
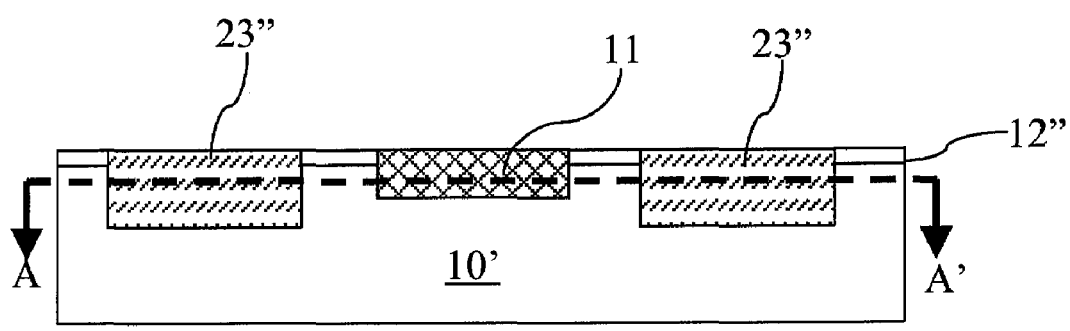

The coats (40', 50', and 60') of the adhesive is subsequently removed as shown in FIGS. 8A-8B. Preferably, an etching chemistry that does not affect the semiconductor material within the region of interest 11 is employed. For example, a wet etch based on ammonium hydroxide (NH$_4$OH) may be utilized to remove an adhesive, for example, a resin cement. After the removal of the adhesive, the prepared sample is mounted on an electron microscopy equipment, for example, a transmission electron microscope, for examination.

While this invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A method of preparing a sample for electron microscopy, comprising:
   etching at least two markers on a top surface of a sample containing at least one metal wiring level, wherein a first marker among said at least two markers is formed on one side of a region of interest and a second marker among said at least two markers is formed on an opposite side of said region of interest;
   filling said at least two markers with a fill material;
   delayering said sample to an upper surface of said region of interest;
   applying a first coat of an adhesive to a delayered surface of said sample and curing said first coat at a temperature from about 70° C. to about 130° C.;
   applying a second coat of said adhesive to said cured first coat and curing said second coat at a temperature from about 70° C. to about 130° C.;
   polishing both sides of said sample, wherein said first marker, said second marker, and said region of interest are polished to a same thickness from 10 nm to 200 nm; and
   removing said adhesive from said sample.

2. The method of claim 1, wherein said fill material is a TEOS oxide.

3. The method of claim 2, wherein said adhesive is a resin cement.

4. The method of claim 1, further comprising applying a third coat of adhesive to the delayered surface of said sample and curing said third coat at a temperature between about 70° C. and about 130° C.

5. The method of claim 1, wherein said sample containing said at least one metal wiring level is delayered prior to said etching such that said sample contains no more than one metal wiring level.

6. A method of preparing a sample for electron microscopy, comprising:
   etching at least two markers on a top surface of said sample, wherein a first marker among said at least two markers is formed on one side of a region of interest and a second marker among said at least two markers is formed on an opposite side of said region of interest;
   filling said at least two markers with a filler material, wherein said filler material is a metal;
   delayering said sample to the upper surface of a region of interest;
   applying at least one coat of adhesive to said delayered sample; and
   polishing both sides of said sample, wherein said first marker, said second marker, and said region of interest are polished to a same thickness from 10 nm to 200 nm.

7. The method of claim 6, wherein said at least two markers have a substantially rectangular cross-sectional opening and have a length in the range from about 1,000 nm to about 4,000 nm, a width in the range from about 70 nm to about 300 nm, and a depth in the range from about 1,000 nm to about 50,000 nm.

8. The method of claim 6, further comprising removing said adhesive from said sample.

9. A method of preparing a sample for electron microscopy, comprising:
   etching at least two markers on the top surface of said sample, wherein a first marker among said at least two markers is formed on one side of a region of interest and a second marker among said at least two markers is formed on an opposite side of said region of interest, wherein said at least two markers have a substantially rectangular cross-sectional opening and have a length in the range from about 1,000 nm to about 4,000 nm, a width in the range from about 70 nm to about 300 nm, and a depth in the range from about 1,000 nm to about 50,000;

filling said at least two markers with a filler material, wherein said filler material is a TEOS oxide deposited by plasma-enhanced chemical vapor deposition (PECVD);

delayering said sample to the upper surface of said region of interest;

applying at least one coat of adhesive to said delayered sample; and polishing both sides of said sample. wherein said first marker, said second marker, and said region of interest are polished to a same thickness from 10 nm to 200 nm.

10. The method of claim 9, further comprising removing said adhesive from said sample.

* * * * *